United States Patent
Ben Chaabane et al.

(10) Patent No.: US 10,822,600 B2
(45) Date of Patent: Nov. 3, 2020

(54) METHOD FOR PRODUCING CELLULASES WITH PRETREATED LIGNOCELLULOSIC POMACE

(71) Applicants: IFP Energies nouvelles, Rueil-Malmaison (FR); ARGO INDUSTRIES RECHERCHE ET DEVELOPPEMENT, Pomacle (FR); INSTITUT NATIONAL DE LA RECHERCHE AGRONOMIQUE, Paris (FR)

(72) Inventors: Mohamed Fadhel Ben Chaabane, Paris (FR); Celine Cohen, Paris (FR)

(73) Assignees: IFP Energies nouvelles, Rueil-Malmaison (FR); AGRO INDUSTRIES RECHERCHE ET DEVELOPPEMENT, Pomacle (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 0 days.

(21) Appl. No.: 16/091,757

(22) PCT Filed: Mar. 24, 2017

(86) PCT No.: PCT/EP2017/057121
§ 371 (c)(1),
(2) Date: Oct. 5, 2018

(87) PCT Pub. No.: WO2017/174378
PCT Pub. Date: Oct. 12, 2017

(65) Prior Publication Data
US 2019/0085310 A1    Mar. 21, 2019

(30) Foreign Application Priority Data
Apr. 8, 2016 (FR) ...................... 16 53124

(51) Int. Cl.
| | | |
|---|---|---|
| *C12P 7/10* | (2006.01) | |
| *C12N 9/42* | (2006.01) | |
| *C12P 21/00* | (2006.01) | |

(52) U.S. Cl.
CPC .............. *C12N 9/2437* (2013.01); *C12P 7/10* (2013.01); *C12P 21/00* (2013.01); *C12P 2201/00* (2013.01); *Y02E 50/10* (2013.01)

(58) Field of Classification Search
None
See application file for complete search history.

(56) References Cited

U.S. PATENT DOCUMENTS

| | | |
|---|---|---|
| 9,249,402 B2 | 2/2016 | Ben Chaabane |
| 9,885,027 B2 | 2/2018 | Ben Chaabane |
| 2011/0262997 A1 | 10/2011 | Smith |

FOREIGN PATENT DOCUMENTS

| | | |
|---|---|---|
| WO | 2007005918 A2 | 1/2007 |
| WO | 2013054005 A1 | 4/2013 |
| WO | 2013087998 A1 | 6/2013 |
| WO | 2015091079 A1 | 6/2015 |

OTHER PUBLICATIONS

International Search Report PCT/EP2017/057121 dated May 12, 2017.
Monschein Mareike et al: "Effect of pretreatment severity in continuous steam explosion on enzymatic conversion of wheat straw: Evidence from kinetic analysis of hydrolysis time courses", Bioresource Technology, Elsevier BV, GB, vol. 200, Oct. 20, 2015 (Oct. 20, 2015), pp. 287-296, XP029312773, ISSN: 0960-8524.
Rosgaard L et al: "Effects of substrate loading on enzymatic hydrolysis and viscosity of pretreated barley straw", Applied Biochemistry and Biotechnology, Humana Press, Inc, United States, vol. 143, No. 1, Oct. 2007 (Oct. 1, 2007), pp. 27-40, XP002668850, ISSN: 0273-2289, [retrieved on Apr. 17, 2007].
Kim Tae Hyun et al: "Bioconversion of sawdust into ethanol using dilute sulfuric acid-assisted continuous twin screw-driven reactor pretreatment and fed-batch simultaneous saccharification and fermentation", Bioresource Technology, Elsevier BV, GB, vol. 130, Dec. 8, 2012 (Dec. 8, 2012), pp. 306-313, XP028980583, ISSN: 0960-8524.
Vera Novy et al: "From wheat straw to bioethanol: integrative analysis of a separate hydrolysis and co-fermentation process with implemented enzyme production", Biotechnology for Biofuels, BIOMED Central Ltd, GB, vol. 8, No. 1, Mar. 18, 2015 (Mar. 18, 2015), pp. 46, XP021215584, ISSN: 1754-6834.

*Primary Examiner* — Heidi Reese
(74) *Attorney, Agent, or Firm* — Millen White Zelano and Branigan, PC; John Sopp

(57) ABSTRACT

The invention relates to a process for producing cellulolytic or hemicellulolytic enzymes comprising
A growth phase a) of a cellulolytic microorganism in a closed reactor, in the presence of at least one carbonaceous growth substrate in a concentration between 10 and 90 g/L, at a temperature of 25-30° C. and a pH of 4-5.5
An enzyme production phase b) in which at least one inducer carbonaceous substrate is added, at a temperature of 25-27° C. and a pH of 4-5, process in which the said inducer substrate is a pretreated pomace obtained from a pretreatment process of lignocellulosic material that has not undergone enzymatic hydrolysis and that is added in fed-batch or continuous mode, and which has particular characteristics: a hydrolysis yield greater than 80% in a test and an apparent viscosity, measured in the test, of less than 1 Pa·s for a shear rate of 10 s−1.

16 Claims, 2 Drawing Sheets

METHOD FOR PRODUCING CELLULASES WITH PRETREATED LIGNOCELLULOSIC POMACE

The invention relates to a process for producing cellulolytic and hemicellulolytic enzymes.

Enzymes are used especially in processes for producing second generation biofuels (i.e. from lignocellulosic biomass), and in particular when the biofuel is ethanol. In general, the process according to the invention can be used in all processes including an enzymatic hydrolysis of biomass, and in particular lignocellulosic biomass. It can be used in particular in the production of enzymes by filamentous fungi.

PRIOR ART

For more than 45 years the conversion of lignocellulosic materials into ethanol, after hydrolysis of the constituent polysaccharides into fermentable sugars, has been the subject of numerous studies.

The lignocellulosic materials are cellulosic materials, that is to say consist of more than 90% by weight of cellulose and/or lignocellulose (the lignocellulose essentially comprises cellulose, hemicellulose and lignin). Celluloses and hemicelluloses are polysaccharides essentially consisting of pentoses and hexoses. Lignin is a macromolecule of complex structure and high molecular weight, based on phenolic compounds.

Wood, straw and maize cobs are the most widely used lignocellulosic materials, but other resources such as dedicated woodland crops, residues of alco-ligneous plants, sugar-containing plants and cereals, lignocellulosic residues from the pulp and paper industry, and products from the conversion of lignocellulosic materials can be used. They comprise for the most part about 35 to 50% of cellulose, 20 to 30% of hemicellulose and 15 to 25% of lignin.

The process for the biochemical conversion of lignocellulosic materials into ethanol includes a physicochemical pretreatment step, followed by an enzymatic hydrolysis step using an enzyme cocktail to produce sugars, a step of ethanolic fermentation of the released sugars, wherein the ethanol fermentation and enzymatic hydrolysis can be carried out simultaneously (SSF process), and an ethanol purification step.

The enzyme cocktail is a mixture of cellulolytic enzymes (also called cellulases) and/or hemicellulolytic enzymes (often called xylanases). Cellulolytic enzymes have three main types of activities: endoglucanases, exoglucanases and cellobiases, the latter also being called β-glucosidases. Hemicellulolytic enzymes have in particular xylanase activities.

Enzymatic hydrolysis is effective and is carried out under mild conditions.

The cost of the enzymes remains very high, accounting for 20 to 50% of the cost of converting the lignocellulosic material into ethanol. As a result, a lot of work has been carried out to reduce this cost: first of all on optimizing the production of enzymes, by selecting the hyperproducing microorganisms and by improving the processes for producing the said enzymes, then on reducing the amount of enzymes in hydrolysis, by optimizing the pre-treatment step, improving the specific activity of these enzymes, and optimizing the implementation of the enzymatic hydrolysis step.

Over the past decade many studies have focused on understanding the mechanisms of action and expression of the enzyme cocktail. The aim is to secrete the most suitable cocktail for the hydrolysis of lignocellulosic materials by modifying the microorganisms.

The cellulolytic microorganism most used for the industrial production of the enzyme cocktail is the fungus *Trichoderma reesei*. It has the ability to secrete in the presence of an inducer carbonaceous substrate, cellulose for example, an enzyme cocktail at very high concentrations (up to 100 g/l). Other proteins possessing properties indispensable for the hydrolysis of lignocellulosic materials are also produced by *Trichoderma reesei*, xylanases for example. The presence of an inducer carbonaceous substrate is essential for the expression of cellulolytic and/or hemicellulolytic enzymes. The nature of the carbonaceous substrate has a strong influence on the composition of the enzyme cocktail. This is the case with xylose, which in an inducer carbonaceous substrate such as cellulose or lactose, enables the activity of the said xylanase to be significantly improved.

Lactose remains one of the most suitable substrates in a process for the industrial production of an enzyme cocktail; however, its cost varies considerably and represents approximately one to two thirds of the cost price of the enzymes. In the case of the use of lactose as a carbon substrate, the enzyme cocktail production process is dependent on an external carbon source. As a result, the use of carbon substrates obtained from the biochemical conversion process of lignocellulosic materials is an important way forward.

Another inducer substrate that can be used is cellulose. However, it is even more expensive than lactose.

Patent application US-2011/262997 replaces the cellulose used in conventional processes for the production of cellulases by pretreated biomass, in particular pretreated by steam explosion under acidic conditions, the biomass optionally having been washed. The pretreated biomass is used only as an inducer, the growth of the microorganism being obtained with glucose as carbon substrate. In the examples of the batch-operated process, the pre-treated (acid-cooked) and washed pomace is added in total at the start of the experiment, as well as a solution of glucose and antifoam agent.

On the one hand this process has the disadvantage that it requires the detoxification of the pre-treated pomace before use. Washings are a suggested option for this. If this process were to be applied on an industrial scale, the implementation of washes would greatly increase the cost of the process.

On the other hand the fact that all the pretreated pomace is added at the start of the experiment greatly increases the viscosity of the medium, which requires the application of high dissipated powers. The power of the motor (kW/m3) required to stir the medium is called "dissipated power". This increase in viscosity also requires very high aeration rates to allow a sufficient oxygen transfer.

Another patent application WO-13/190064 also relates to the production of enzymes for the enzymatic hydrolysis of pretreated lignocellulosic biomass (called 1st pretreated biomass). This production is carried out in the absence of added sugar (such as glucose), but in the presence of a solid comprising complex sugars and lignin. This solid is preferably obtained from a different biomass treatment process, which comprises the enzymatic hydrolysis then the separation of the said solid, the process starting from a $2^{nd}$ pretreated biomass. In this process for producing enzymes it is essential that the ratio of complex sugars to lignin of the said solid is less than the ratio of complex sugars to lignin of the said $2^{nd}$ biomass. This criterion requires removing at least 50% of the water and soluble sugars from the hydrolysate. This increases the cost of the process. Furthermore, this solid has a very high percentage of lignin, which makes the production of enzymes less efficient. In fact, it is known that the phenolic compounds of lignin have an inhibitory effect on the enzymes.

The patent application WO-13/053924 operates with a process of the same type, in which the pretreated biomass also plays the role of growth substrate, without the addition (or with slight addition) of simple sugar (glucose). Moreover, the culture is carried out without the addition of vitamins and/or minerals and/or enzyme production inducers. This process also requires the detoxification of the pomace (especially if the pretreatment used is acidic).

The patent application WO 011028554 teaches the use of the solid residue obtained from the hydrolysis of hemicelluloses for the production of cellulases by *Trichoderma reesei*, in which the residue has been stripped of its lignin fraction in a lignin extraction step. The production is carried out in the presence of an addition of sugars (glucose). The enzymes obtained are used for the hydrolysis of cellulose, and not for the hydrolysis of hemicellulose. The delignified solid residue is used at the start of the growth phase of the microorganism, which causes operating difficulties.

An object of the invention is to propose an inducer carbon source obtained from the production process and enabling an enzyme cocktail to be produced that is suitable for the hydrolysis of the lignocellulosic material.

The cellulase production process uses a pretreated pomace that has preferably not been previously detoxified.

DETAILED DESCRIPTION OF THE INVENTION

The present invention relates to a process for producing an enzyme cocktail in submerged culture by a cellulolytic microorganism that uses a pretreated pomace.

"Pre-treated pomace" refers to the substrate derived from lignocellulosic materials that has undergone a pretreatment step, preferably a steam explosion in an acidic medium. The biomass is a type of preferred material; in the text the terms biomass and lignocellulosic material are often used interchangeably.

A process for biochemical conversion of lignocellulosic materials to alcohol (in particular ethanol) generally comprises a physicochemical pretreatment step (preferably a steam explosion in an acidic medium), producing a pre-treated pomace, followed by an enzymatic hydrolysis step using an enzyme cocktail producing sugars, then an ethanolic fermentation step of the said sugars, wherein the ethanol fermentation and the enzymatic hydrolysis can be carried out simultaneously (SSF process) or separately (SHF process), and finally a purification step of the ethanol.

The invention has many advantages:
it reduces or even eliminates the supply of carbonaceous substrate of external origin to the said process for biochemical conversion of lignocellulosic materials.
it produces an enzyme cocktail particularly adapted to the enzymatic hydrolysis of the pretreated lignocellulosic material in the biochemical conversion process.
it proposes a process for carrying out the process which makes it possible not to have to detoxify (for example to wash) the pretreated pomace used. This enables the amount of effluent produced during washing and that has to be reprocessed before discharge to be reduced.
it proposes a process in which the viscosity of the medium is kept at a low value, which limits the oxygen demand and thus provides a process that can be scaled-up to an industrial level.

The process can be operated in continuous or fed-batch mode.

In fed-batch mode, a particularly advantageous way of carrying out the process is to carry out the addition of the pomace in a sequential manner depending on the change in the pH of the reaction medium and % $CO_2$ in the output gases.

This mode of operation allows the use of non-detoxified pre-treated pomace (unwashed pomace).

An advantage of this process, and particularly with the above mode of operation, is to maintain a low viscosity of the medium. This is important not to affect the oxygen transfer and to have a process that can be scaled-up to an industrial level.

The invention more particularly relates to an enzyme production process comprising two phases:
a growth phase a) of the said microorganism in the presence of at least one carbonaceous growth substrate, in a closed reactor, the said growth phase being carried out with a concentration of carbonaceous growth substrate of between 10 and 90 g/l. The pretreated pomace is not introduced in this phase. A culture of the said microorganism is thus obtained.
a phase b) for producing the enzyme (or enzymes) cocktail, in which at least one inducer carbonaceous substrate is fed-batch or continuously, the said inducer carbonaceous substrate being a part of the said pretreated pomace, the said production phase being carried out with a continuous or discontinuous addition (fed-batch) of the pomace.

More specifically, the invention relates to a process for producing cellulolytic or hemicellulolytic enzymes comprising:
a growth phase a) of a cellulolytic microorganism in a closed reactor, in the presence of at least one carbonaceous growth substrate at a concentration of between 10 and 90 g/l, at a temperature of 25-30° C. and a pH of 4 to 5.5,
an enzyme production phase b) in which at least one inducer carbonaceous substrate is introduced at a temperature of 25-27° C. and a pH of 4-5,
process in which
the said inducer substrate is a pretreated pomace obtained from a pretreatment process of lignocellulosic material, the said pomace not having undergone enzymatic hydrolysis and being introduced in fed-batch or continuous mode,
the said pomace shows an enzymatic hydrolysis yield of at least 80% after 96 h, the said hydrolysis being conducted at 50° C. and pH 4.8 on the said pomace containing 15 wt. % of dry matter (DM) with 10 mg of CELLIC®CTEC2 enzymes per gram of MS, the said yield being the ratio of the mass of simple sugars released by the enzymatic hydrolysis divided by the theoretical maximum mass that would be obtained if all the cellulose, hemicelluloses and oligomers resulting from the pretreatment were hydrolysed,
the said pre-treated pomace suspended at room temperature at 10 wt. % of DM has an apparent viscosity of less than 1 Pa·s at a shear rate of 10 $s^{-1}$, preferably less than 0.15 Pa s.
the said pomace is introduced at a rate of between 0.3 and 0.8 gram of MS per litre of medium and per hour in continuous mode; in fed-batch mode the amount of pomace added every f hours, f being between 0.5 h and 48 h, is between 0.3 f and 0.8 f grams of dry matter per litre of medium.

Preferably, the apparent viscosity of the medium of step b) remains less than 10 Pa·s at a shear rate of 10 s$^{-1}$, preferably less than 1 Pa·s.

The pomace may have been detoxified (washed) before being introduced into phase b) or may not have been detoxified (washed). Phase b) generally operates in the absence of added sugar. Thus, very advantageously, the said pretreated pomace is the only inducer substrate.

As will be explained in detail below, the pretreated pomace is formed of a liquid and a solid, in which the solid contains 20-70% of dry matter, of which 20-50% is lignin. The solid of the said pretreated pomace also contains 30-60 wt. % of cellulose and 1-10 wt. % of mineral compounds and hemicellulose, and the liquid contains 30-80 wt. % of sugars.

The pretreatment is preferably a steam explosion under acidic conditions.

Phase a)

The microorganisms used in the process for producing an enzyme cocktail according to the invention are strains of fungi belonging to the genera *Trichoderma, Aspergillus, Penicillium* or *Schizophyllum*, preferably belonging to the species *Trichoderma reesei*. The most effective industrial strains are strains belonging to the species *Trichoderma reesei*, modified so as to improve the enzyme cocktail by mutation-selection processes, such as for example the strain CL847 (French patent FR-2555803). Strains improved by genetic recombination techniques can also be used. These strains are cultured in stirred and aerated reactors under conditions compatible with their growth and the production of the enzymes. Numerous improved strains are known, such as MCG77 (Gallo—U.S. Pat. No. 4,275,167), MCG 80 (Allen, A L and Andreotti, R E, Biotechnol-Bioengi 1982 12, 451-459 1982), RUT C30 (Montenecourt, B S and Eveleigh, D E, Appl. Environ. Microbiol. 1977, 34, 777-782) and CL847 (Durand et al, 1984 Proc. SFM Symposium "Genetics of Industrial Microorganisms", Paris, HESLOT H. Ed, pp 39-50).

The carbonaceous growth substrate of the said microorganism used in the said phase a) is advantageously chosen from soluble industrial sugars, and preferably from glucose, lactose, xylose, liquid residues (distillery residues) obtained after ethanolic fermentation of the monomeric sugars of the enzymatic hydrolysates of lignocellulosic materials and extracts of the hemicellulosic fraction (C5 compounds) in the form of monomers obtained from pretreated lignocellulosic substrate (such as the liquid separated at the pretreatment stage), used alone or as a mixture. Depending to its nature, the said carbon substrate is introduced into the closed reactor before sterilisation or is sterilised separately and introduced into the closed reactor after sterilisation of the latter.

This carbonaceous growth substrate is used in the said phase a) at an initial concentration of between 10 and 90 g of carbonaceous substrate per litre of reaction volume.

Preferably the said growth phase a) is carried out over a period of between 30 and 70 hours, preferably between 30 and 40 hours.

Preferably the said growth phase a) operates at a pH between 4 and 5.5, and preferably 4.8, and at a temperature between 25 and 30° C., and preferably 27° C.

Phase b)

According to the invention, the said inducer carbonaceous substrate used in the said production phase b) is advantageously a pretreated pomace.

The pretreatment step of the lignocellulosic material enables the susceptibility of the cellulosic fraction to enzymatic hydrolysis to be improved.

Preferably, the pretreatment step is carried out in an acidic medium. It is preferably an acid hydrolysis, an acid cooking or a steam explosion. Preferably, the pretreatment step is the steam explosion. Advantageously, the steam explosion is preceded by a step of impregnating the said lignocellulosic material with an acid solution, which is preferably an aqueous solution of sulphuric acid. This is then called steam explosion under acidic conditions (the material contains acid).

At the end of the pretreatment, a pretreated pomace is obtained and a part of this pomace is taken for the production of enzymes, the other part is sent to enzymatic hydrolysis and then to fermentation for the production of alcohol.

The said part of the pomace may be used as such (whole pomace) or, preferably, it may be its solid part or also advantageously a portion obtained after more or less significant separation of liquid.

According to the pretreatment used, the pomace is in solid form with more or less moisture but without liquid phase, or it contains solid and liquid phases, and in the latter case the liquid phase can be separated in whole or in part.

Depending on the pretreatment process used, the solid part represents between 20 and 70% of the weight of the pretreated pomace. The pomace used for the production of enzymes has a dry matter content of 10-85%, most often 20-70%, and very preferably 40%-60% (which often corresponds to obtaining a pomace in solid form after the pretreatment).

The solid part consists of lignin, mineral compounds, cellulose, and non-hydrolysed residual hemicellulose. The proportion of cellulose in the said solid part is 30 to 60 wt. The proportion of lignin in the said solid part is 20 to 50 wt. %. The proportion of mineral compounds and hemicellulose in the said solid portion is 1 to 10 wt. %.

The liquid portion of the said pretreated pomace contains xylose, xyloligosaccharides, mannose and arabinose in proportions of between 30 and 80%.

In a preferred embodiment the pomace is used directly, that is to say without undergoing chemical or biochemical treatment. Thus, the invention does not use a pretreated pomace which has also undergone enzymatic hydrolysis. One or more physical treatments are possible (separation of liquid, heating, concentration means, etc.).

In a preferred mode, the pomace is unwashed. In some cases it can be washed to detoxify it, preferably using a minimal amount of water.

Preferably the said production phase b) is carried out over a period of between 70 and 200 hours, preferably between 100 and 150 hours.

Preferably the said production phase b) operates at a pH of between 4 and 5 and at a temperature of 25 to 27° C.

At the end of the pretreatment step the pretreated pomace is used directly or not in the production phase b) of the enzyme cocktail according to the invention as inducer carbonaceous substrate.

The production phase b) is carried out either in continuous mode by a continuous addition of the pomace at a rate of between 0.3 and 0.8 gram of dry matter per litre of medium and per hour (preferably from 0.4 to 0.6 g/L/h and most often 0.5 g/L/h), or in fed-batch mode by a sequential addition of the pomace every f hours, f being between 0.5 hours and 48 hours, the amount of pomace added being between 0.3 f and 0.8 f gram of dry matter per litre of medium.

This means that if, for example, the addition is made every 12 h, the amount of added pomace will be between 3.6

(i.e. 0.3×12) and 9.6 (i.e. 0.8×12) g of dry matter per litre of medium, preferably between 4.8 and 8.4 g of dry matter per litre of medium.

According to a preferred mode of conduct of the fed-batch, the addition of pretreated pomace is carried out depending on the signal of the mol. % CO2 in the exit gases and the pH measurement of the medium. A stabilisation of the % $CO_2$ at ±0.02% (for a vvm of 0.5 $min^{-1}$) coupled with a pH increase of 0.05 unit or an increase of the $pO_2$ of at least 5% triggers the sequential addition of pomace.

In fact, following an addition there is an increase in % $CO_2$ in the exit gases, which corresponds to the consumption of soluble sugars present in the pretreated pomace (essentially xylose and glucose). Then the enzymes attack the cellulose, which will induce the production of cellulases, and the % $CO_2$ decreases.

The addition is carried out when a decrease in % $CO_2$ in the exit gases and a pH increase of more than 0.05 units are observed.

The pO2 (partial pressure of dissolved oxygen) is generally kept high (above 30% of the oxygen saturation partial pressure in the liquid medium at atmospheric pressure).

When carrying out the process, it will advantageously be ensured that the apparent viscosity of the medium remains below 10 Pa·s at a shear rate of 10 $s^{-1}$, preferably below 1 Pa·s.

In fact, the viscosity adversely affects the transfer of oxygen. It is then necessary to greatly increase the dissipated power and/or the aeration rate to ensure the transfer, which greatly increases the energy expenditure and can make the process difficult to scale-up to an industrial level.

The pretreated pomace that can be used in the process according to the invention has the following characteristics:
- in the enzymatic hydrolysis test carried out with a sample of the said pomace restored to 15% of dry matter (DM), with 10 mg of CELLIC® CTEC2 enzymes (marketed by Novozymes) per gram of MS, at 50° C. and pH 4.8, after 96 hours the hydrolysis yield is greater than 80%. The hydrolysis yield is the ratio of the mass of simple sugars (such as glucose, xylose) released by the enzymatic hydrolysis divided by the theoretical maximum mass which would be obtained if all the cellulose, hemicelluloses and oligomers resulting from the pretreatment were hydrolysed,
- in the viscosity test, in suspension with 10% DM, pretreated pomace has an apparent viscosity of less than 1 Pa·s, and preferably less than 0.15 Pa·s, for a shear rate of 10 s. 1. The measurement is carried out with an AR2000 rheometer from TA Instrument with a helical ribbon-type geometry as described in the article "Experimental guidelines to optimize two crucial steps of lignocellulosic bioethanol production: a rheological approach" by Hénault et al. 2014.

The nature of the biomass as source of the pretreated pomace has an influence on the production of enzymes, and also on the enzymatic hydrolysis performance of the biochemical process for treating lignocellulosic biomass. The examples show that miscanthus is more reactive than straw, the latter nevertheless producing performance of a high level in the process according to the invention.

EXAMPLES

The examples demonstrate that the mode of conduct and the type of pomace used have an influence on the performance of the process.

Example 1: Use of the Pretreated Pomace in Batch Mode: All the Pomace is Added at the Start of the Experiment The preculture of the fungus is carried out in a mechanically stirred fermenter. The mineral medium has the following composition: KOH 1.66 g/l, $H_3PO_4$ 85% 2 mL/L, $(NH_4 2SO_4$ 2.8 g/L, $MgSO_4 \cdot 7H_2O$ 0.6 g/L, $CaCl_2$ 0, 6 g/L, $MnSO_4$ 3.2 mg/L, $ZnSO_4 \cdot 7H_2O$ 2.8 mg/L, $CoCl_2$ 4.0 mg/L, $FeSO_4 \cdot 7H_2O$ 10 mg/L, corn steep 1, 2 g/L, defoaming agent 0.5 mL/L and addition of potassium phthalate at a concentration of 5 μL–1 to buffer the pH.

The fermenter containing the mineral medium is sterilised at 120° C. for 20 minutes.

The fermenter is seeded with the strain of *Trichoderma reesei* CL847.

Growth of the mushroom in preculture is carried out using glucose as a carbon substrate at a concentration of 30 gL–1. The growth of the inoculum lasts 2-3 days and is performed at 28° C. in an incubator shaker.

The transfer to the cellulase production fermenter is carried out when the residual glucose concentration is less than 15 g/L.

Four experiments were carried out to produce enzymes using miscanthus pretreated by steam explosion under acid conditions:
- 2 experiments carried out at 10% DM
- 2 experiments carried out at 20% DM The production of cellulases is carried out in a mechanically shaken fermenter. The mineral medium has the following composition: KOH 1.66 g/l, $H_3PO_4$ 85% 2 mL/L, $(NH_4)2SO_4$ 2.8 g/L, MgSO4, 7H20 0.6 g/L, $CaCl_2$ 0.6 g/L, MnSO4 3.2 mg/L, $ZnSO_4$, $7H_2O$ 2.8 mg/L, $CoCl_2$ 4.0 mg/L, $FeSO_4$, 7 H2O 10 mg/L, corn steep 1, 2 g/L, antifoaming agent 0.5 mL/L.

The fermenter containing the mineral medium is sterilised at 120° C. for 20 minutes.

The fermenter is inoculated at a concentration of 10% (v/v) with a liquid preculture of the strain of *Trichoderma reesei* CL847. The pH is adjusted to 5.5

The experiments carried out at 20% DM were unsuccessful: there was no production of cellulases. The medium was too viscous and/or contained too many inhibitors.

The experiments carried out at 10% DM produced 15 g/L of protein after 150 hours, i.e. a productivity of 0.1 g/L/h.

Figure 1:
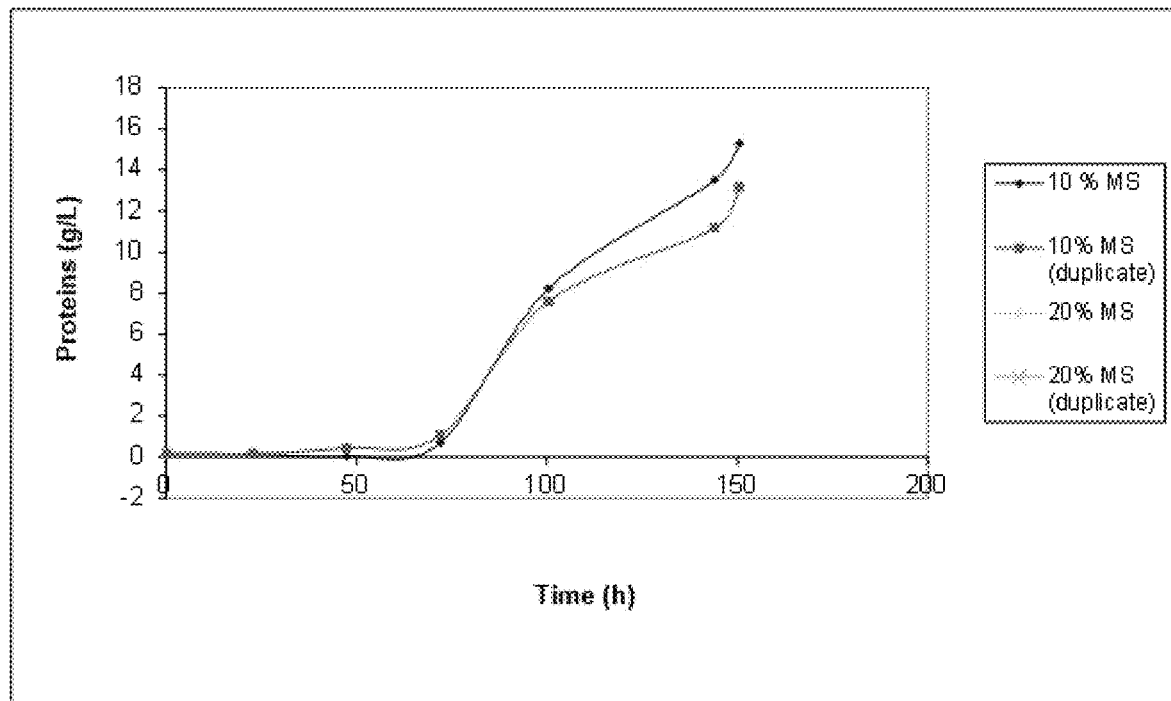
FIG. 1 shows the evolution of the protein concentration in batch mode with pretreated lignocellulosic biomass under acidic conditions.

The evolution of the protein concentration in batch mode with pretreated lignocellulosic biomass under acidic conditions is illustrated in FIG. 1.

Example 2: Experiments in Fed-Batch Mode

Five experiments were carried out (Exp. 1 to 5).

The preculture of the fungus *Trichoderma reesei* CL847 is carried out as in Example 1, but with 15 g/L of glucose as the only carbon substrate. Cellulase production starts after 24 hours by adding the pretreated pomace in fed-batch mode, that is to say by adding 6 g of pomace dry matter per litre of medium every 12 hours (Exp. 3, Exp. 4, Exp. 5), or 12 g of dry matter per litre with the same frequency (Exp. 1 and Exp. 2).

The five experiments were carried out using three different lignocellulosic substrates pretreated by steam explosion under acidic conditions and obtained as such (no liquid separation):

Miscanthus 1 responding to the hydrolysis test and the viscosity test (apparent viscosity at $10\ s^{-1}$ equal to 0.09 Pa·s) (Exp. 1 and Exp. 5)

Miscanthus 2 not responding to the hydrolysis test (yield <70%) (Exp. 2 and Exp. 3)

Wheat straw 1 responding to the hydrolysis test and the viscosity test (apparent viscosity at $10\ s^{-1}$ equal to 1.1 Pa·s) (Exp. 4)

The hydrolysis and viscosity tests are those described above.

FIG. 1 shows the evolution of the protein concentration of various experiments carried out with the said pomaces:

Exp. 1: Pomace miscanthus 1—procedure with a quantity of pomace twice as large as in the optimal procedure Exp. 2: Pomace miscanthus 2—procedure with a quantity of pomace twice as large as in the optimal procedure Exp 3: Pomace miscanthus 2—so-called optimal procedure Exp 4: Pomace wheat straw 1—so-called optimal procedure Exp 5: Pomace miscanthus 1—so-called optimal procedure The so-called optimal procedure protocol for the production of cellulases, used in Exp. 3, 4 or 5, is as follows:

After a growth phase of 24 hours in batch mode with glucose at 15 g/L, additions of miscanthus pomace were made about every 12 hours with an addition of 6 g of dry matter per litre of medium. After 120 h, the frequency of the additions was adjusted according to the $CO_2$ signal.

In fact, following an addition there is an increase in % $CO_2$ in the exit gases (FIG. 3), which corresponds to the consumption of soluble sugars present in the pretreated pomace (mainly xylose and glucose). Then the enzymes attack the cellulose that will induce the production of cellulases (FIG. 2) and the % $CO_2$ decreases.

The addition is carried out when a decrease in the % $CO_2$ in the exit gases and a pH increase of more than 0.05 unit are observed.

The p02 signal (concentration of dissolved oxygen at saturation) is kept high (above 30%) throughout the experiment with a low dissipated power (less than 1 kW/m3).

In FIG. 1 the pomace is added when the pH rises and the $CO_2$ stops falling at a rate of 6 g of dry matter per litre per addition. The arrow corresponds to the time when the pomace is added.

Figure 2:
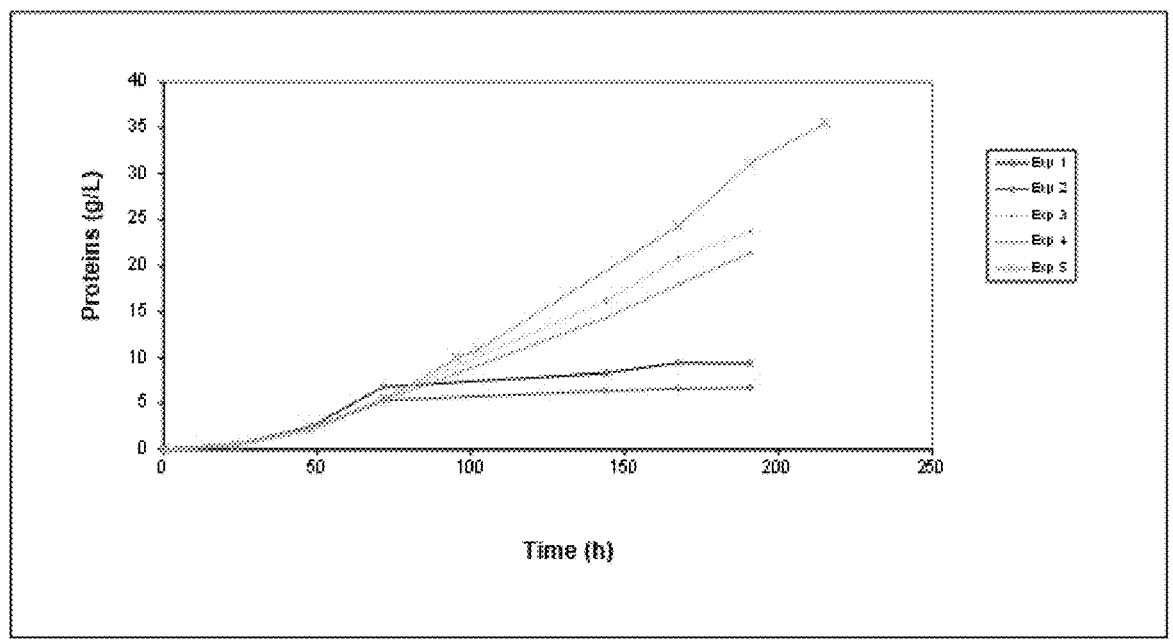
FIG. 2 shows the results on protein concentration based on the procedure mode and the type of pomace used.
Figure 3:
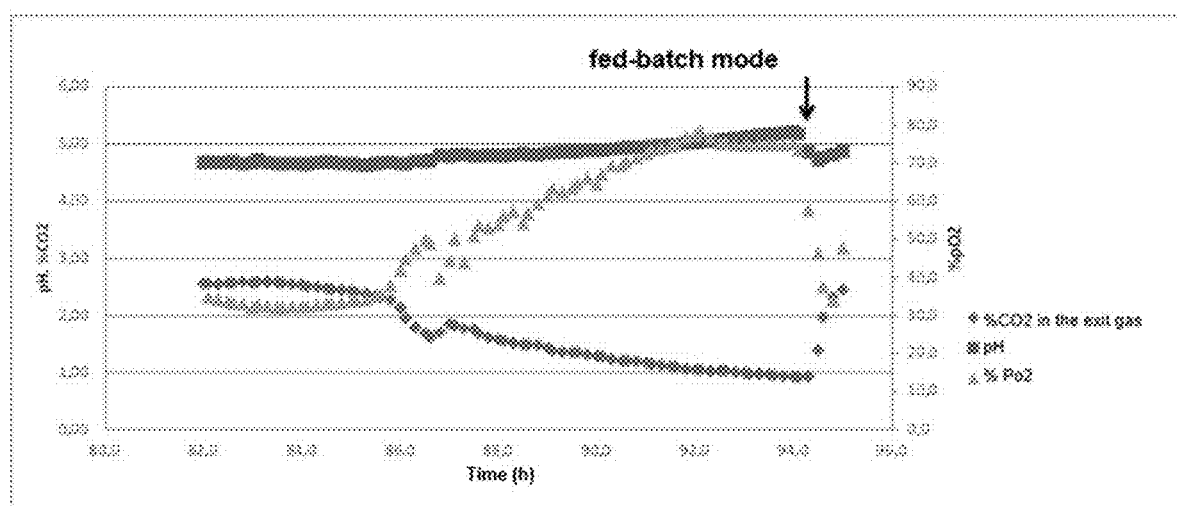
FIG. 3 shows the pH, % $CO_2$ and % $pO_2$ in the exit gases.

The results are plotted in FIG. 2 and show the importance of both the procedure mode and the type of pomace used on the performance of the process.

In fact, the optimal process (Exp. 5 of FIG. 2) enables a final concentration of cellulases of 35 g/L in 210 h to be achieved, i.e. a productivity of 0.17 g/L/h.

It is therefore 70% better than that obtained in batch mode shown in Example 1.

The other experiments with the same fed-batch rate (optimal procedure) but using a pretreated straw 1 (responding to the tests) (Exp. 4) or miscanthus 2 (not responding to the tests) (Exp. 3) resulted in a productivity 32% and 25% lower, respectively, than that of Exp. 5.

Experiments with fed-batch rates that were twice the optimal rate resulted in poor production performances either with the pretreated miscanthus 1 responding to the tests (Exp. 1) or with the pre-treated miscanthus 2 not responding to the tests (Exp. 2).

In these experiments it was found that the $pO_2$ fell below 10%. The pretreated straw used has an apparent viscosity of the material in suspension that is about 12 times greater than that of miscanthus, which may explain the decrease in $pO_2$.

The invention claimed is:

1. Process for producing cellulolytic or hemicellulolytic enzymes comprising:

conducting a growth phase a) of a cellulolytic microorganism in a closed reactor, in the presence of at least one carbonaceous growth substrate at a concentration of between 10 and 90 g/l, at a temperature of 25-30° C. and a pH of 4-5.5, and conducting an enzyme production phase b) to produce an enzyme medium in which at least one inducer carbonaceous substrate is introduced at a temperature of 25-27° C. and a pH of 4-5, wherein said inducer carbonaceous substrate is a pretreated pomace obtained from a pretreatment process of lignocellulosic material, said pomace not having undergone enzymatic hydrolysis and being introduced into the closed reactor in fed-batch or continuous mode, said pretreated pomace, when suspended at room temperature at 10 wt. % of DM, has an apparent viscosity of less than 1 Pa·s at a shear rate of $10\ s^{-1}$, said pomace is introduced at a rate of between 0.3 and 0.8 gram of dry matter ("DM") per litre of medium and per hour when in continuous mode; or, when in fed-batch mode, the amount of pomace added every f hours, f being between 0.5 h and 48 h, is between 0.3f and 0.8f grams of dry matter per litre of medium.

2. Process according to claim 1, wherein the apparent viscosity of the enzyme medium in the enzyme production phase b) remains less than 10 Pa·s at a shear rate of $10\ s^{-1}$.

3. Process according to claim 1, wherein the pomace has been washed before being introduced.

4. Process according to claim 1, wherein the pomace has not been washed before being introduced.

5. Process according to claim 1, wherein the said cellulolytic microorganism is a fungus of the species *Trichoderma reesei*.

6. Process according to claim 1, wherein the pretreatment is a steam explosion under acidic conditions.

7. Process according to claim 1, wherein the enzyme production phase b) is conducted in the absence of added sugar.

8. Process according to claim 1, wherein the said pretreated pomace is the only inducer substrate used in enzyme production phase b).

9. Process according to claim 1, wherein said pretreated pomace is formed of a liquid and a solid, and the solid contains 20-70% dry matter, of which 20-50% is lignin.

10. Process according to claim 1, wherein said pretreated pomace is formed of a liquid and a solid, and the solid of said pretreated pomace contains 30-60 wt. % of cellulose and 1-10 wt. % of mineral compounds and hemicellulose, and the liquid contains 30-80 wt. % of sugars.

11. Process according to claim 1, wherein, in the enzyme production phase b) in which the pomace is added, the $pO_2$ partial pressure of dissolved oxygen in the enzyme medium at atmospheric pressure is maintained greater than 30% of the oxygen saturation partial pressure.

12. Process according to claim 1, wherein the pretreated pomace is part of the pretreated pomace resulting from a lignocellulosic biomass pretreatment step, and another part of the pretreated pomace is introduced into an enzymatic hydrolysis step carried out in presence of the enzymes obtained by said enzyme production phase b), the hydrolysate obtained being passed to an ethanolic fermentation step, and the effluent obtained being distilled in order to separate the ethanol.

13. Process according to claim 12, wherein the part of the pretreated pomace resulting from a lignocellulosic biomass pretreatment step is used directly in enzyme production phase b).

14. Process according to claim 12, wherein a part or all of the liquid contained in the part of the pretreated pomace resulting from a lignocellulosic biomass pretreatment step is separated, and the resulting pomace obtained is introduced into enzyme production phase b).

15. Process according to claim 1, wherein said pre-treated pomace, when suspended at room temperature at 10 wt. % of DM, has an apparent viscosity of less than 0.15 Pa·s at a shear rate of 10 $s^{-1}$.

16. Process according to claim 1, wherein the apparent viscosity of the enzyme medium in the enzyme production phase b) remains less than 1 Pa·s at a shear rate of 10 $s^{-1}$.

* * * * *